(12) United States Patent  
Caillouette et al.

(10) Patent No.: US 8,425,618 B2  
(45) Date of Patent: Apr. 23, 2013

(54) HIP REPLACEMENT PROCESS

(76) Inventors: James Thompson Caillouette, Laguna Beach, CA (US); Farid Bruce Khalili, Briarcliff Manor, NY (US)

( * ) Notice: Subject to any disclaimer, the term of this patent is extended or adjusted under 35 U.S.C. 154(b) by 222 days.

(21) Appl. No.: 12/661,080

(22) Filed: Mar. 9, 2010

(65) Prior Publication Data

US 2011/0224798 A1   Sep. 15, 2011

(51) Int. Cl.
*A61F 2/36*   (2006.01)
(52) U.S. Cl.
USPC ..................................... 623/22.42; 623/22.46
(58) Field of Classification Search ............... 623/22.11, 623/22.4–22.46, 23.15, 22.15, 23.17–23.38; 606/89
See application file for complete search history.

(56) References Cited

U.S. PATENT DOCUMENTS

| | | | |
|---|---|---|---|
| 4,846,839 A | 7/1989 | Noiles | |
| 4,957,510 A | 9/1990 | Cremascoli | |
| 6,083,263 A | 7/2000 | Draenert et al. | |
| 6,306,174 B1 | 10/2001 | Gie et al. | |
| 7,641,698 B1 | 1/2010 | Gibbs et al. | |
| 2004/0078083 A1* | 4/2004 | Gibbs et al. | 623/22.17 |
| 2006/0229732 A1 | 10/2006 | Bachelier | |
| 2007/0050039 A1* | 3/2007 | Dietz et al. | 623/19.13 |
| 2010/0249943 A1* | 9/2010 | Bergin et al. | 623/22.42 |

\* cited by examiner

*Primary Examiner* — Thomas J Sweet  
*Assistant Examiner* — Megan Wolf  
(74) *Attorney, Agent, or Firm* — William W. Haefliger

(57) ABSTRACT

In a human hip replacement process, the steps include providing a selected size generally longitudinally extending stem and laterally angled neck, the stem received endwise into a recess in an elongated femur, there being a ball on the neck, the neck and stem having a non-circular tongue and groove interfit connection to resist relative rotary displacement therebetween, the connection defining a generally longitudinal axis, fitting the ball in a socket on a hip bone, to pivot in the socket, the selection of stem and neck, and tongue and groove connection between the size selected stem and neck, enabling accurate pivoting of the ball. A set of different size balls and neck units are enabled for selective choice, as during surgery.

13 Claims, 15 Drawing Sheets

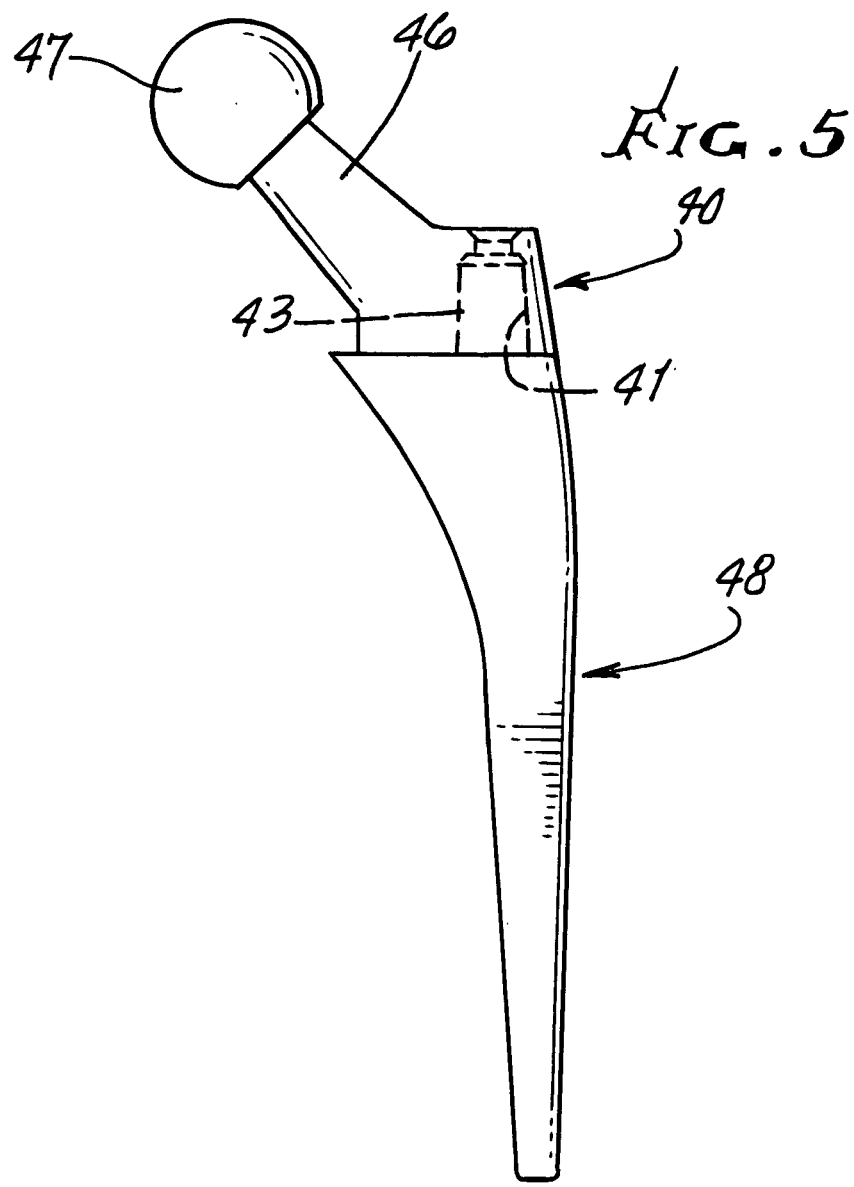
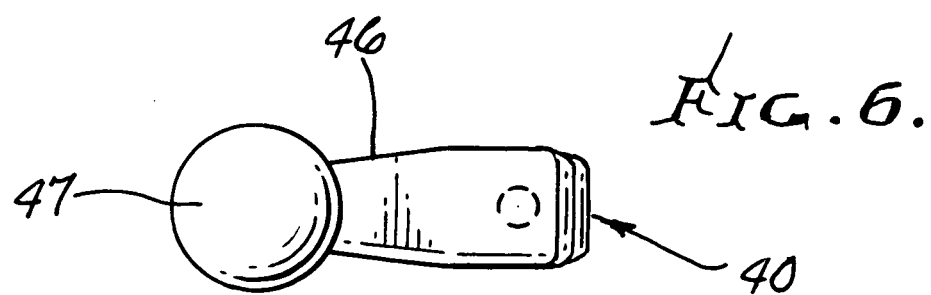

2-NECK ANGLE CHANGE

PARALLEL NECK SLIDE

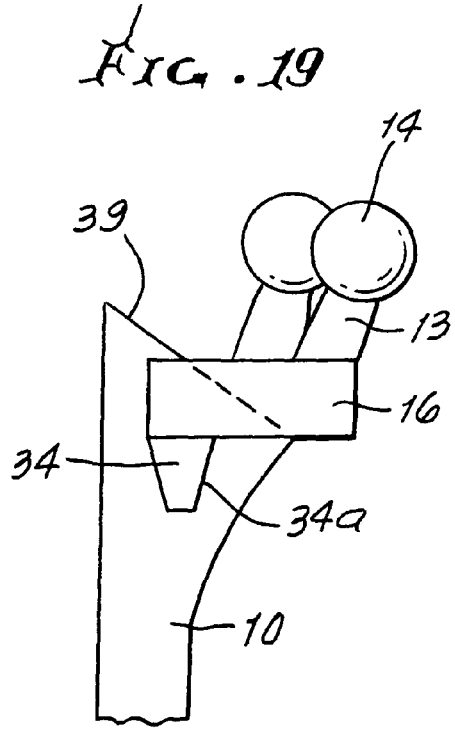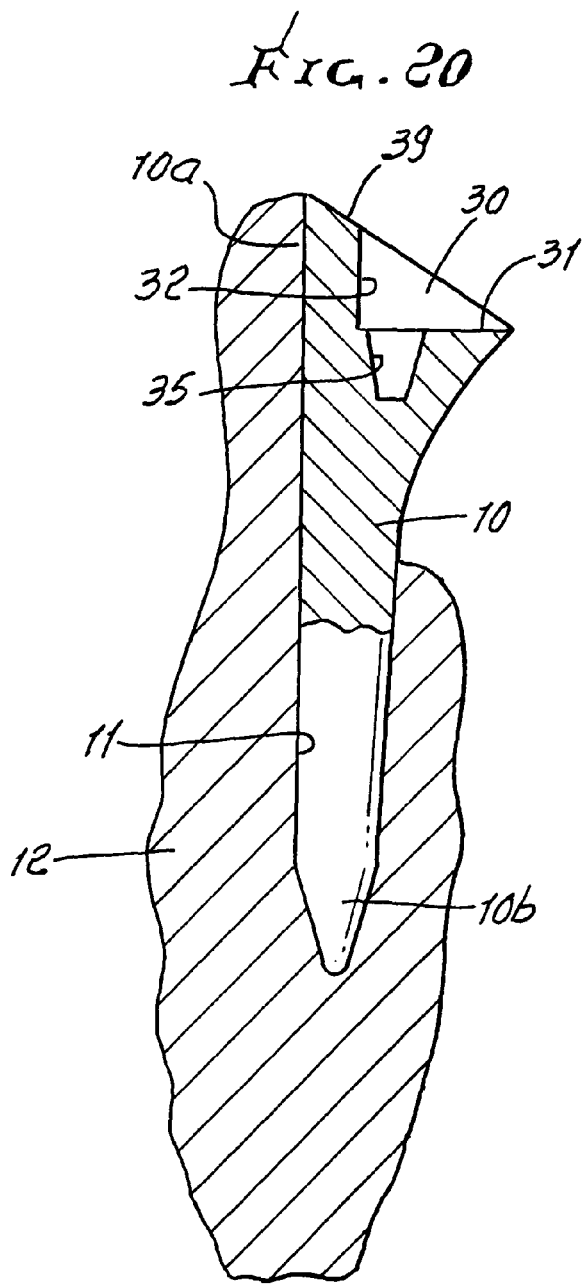

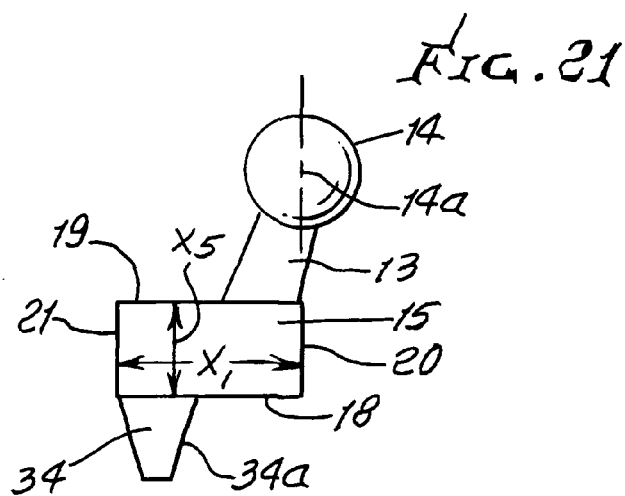
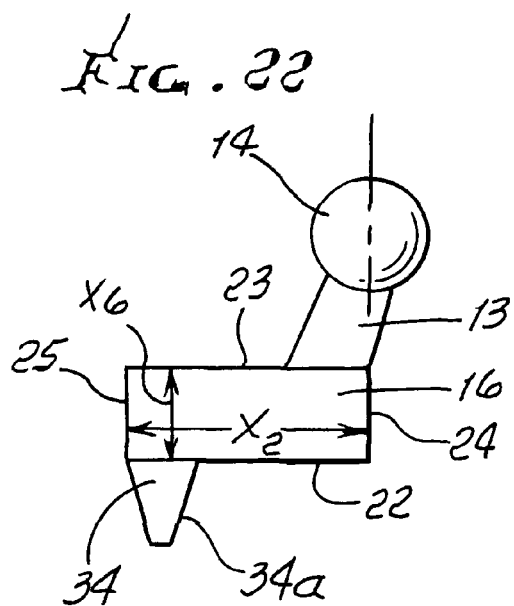
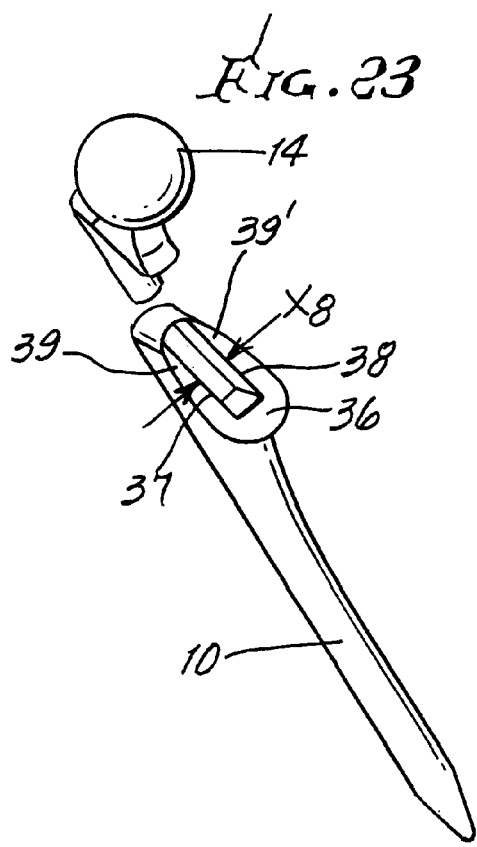

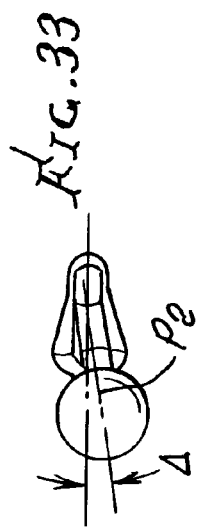
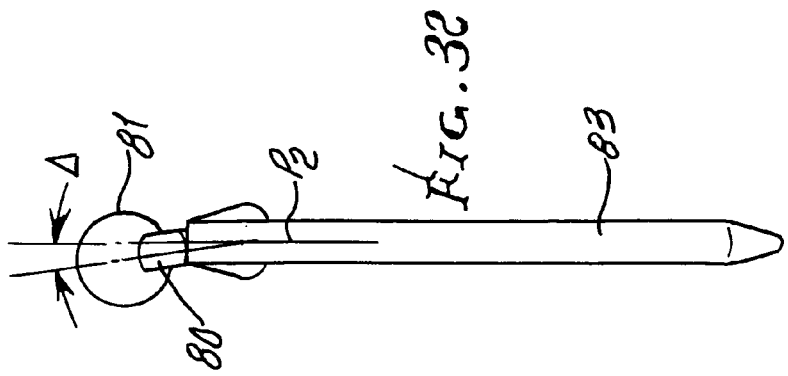
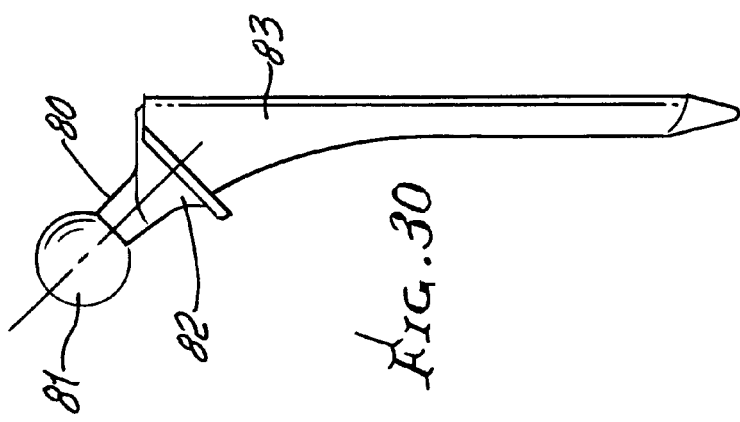
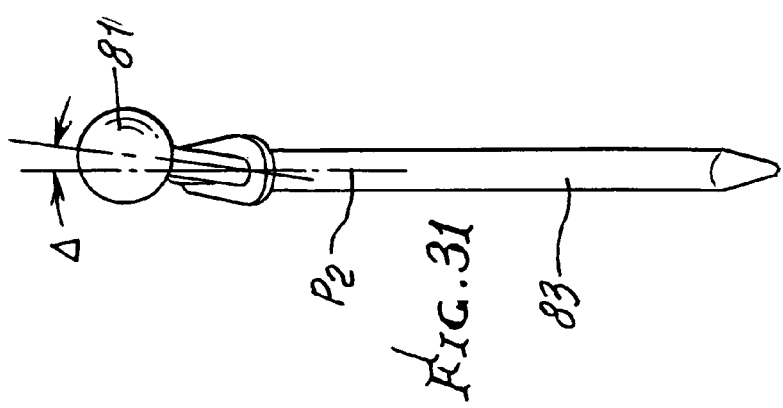

HIP REPLACEMENT PROCESS

BACKGROUND OF THE INVENTION

This invention relates generally to human hip replacement, and more particularly to achieving more accurate leg length restoration and joint stability, as during surgery. The invention concerns implantable orthopedic prostheses for total hip replacement and, more particularly, a prosthesis which receives a modular neck assembly selected for a desired anteversion, neck length, neck angle and offset.

During such surgery, a replacement stem is employed and inserted lengthwise into a pathway in the femur. The stem carries an angularly extending i.e. offset neck, and a ball at the neck terminus, to be received into a socket defined by the joint. These components must be accurately relatively positioned to accommodate to each patient's particular femur and hip socket configuration, as during surgery, which is time consuming and subject to adjustment problems and difficulties. It is found that the stem may not seat at a local predicted by the surgery, and that dislocation may occur resulting from use of decreased offset (lateral neck spacing between ball and stem), and/or from positioning the stem such that the neck does not well align with the socket. Avoiding such dislocation may result in undesired compromises between desired leg length (determined by degree of stem insertion into the femur recess) and overall joint stability.

More specifically, in hip replacement surgery, the natural head and neck portion of the femur are removed and replaced with a metallic hip prosthesis called a stem. The stem is inserted in a cavity formed in the femur. This prosthesis generally comprises three elements: a distal stem portion for fixation into the distal part of the femur, a proximal body portion for fixation in the metaphysis of the femur, and a neck portion for replacing the natural femoral neck which is formed at an angle to the stem. These elements can be connected and configured in numerous ways, but generally these elements form either a one-piece stem design or a modular stem design. The neck typically has a male taper at its free proximal end and is mated with a spherical ball (head) that has a female taper machined into it. The surgeon can choose heads of various diameters with either deeper or shallower tapers to adjust neck length. The head is mated with a socket in the hip. Every patient requires some degree of fitting due to the unique anatomical requirements of the particular patient. Also, often, the stem is either inserted too far or too short into the femur, many times because of the mismatch between the broach that prepares the femur to receive the stem and the stem. If the stem is inserted too far into the femur, then the leg length is shortened. On the other hand, if the stem is not inserted far enough into the femur, then the leg length is lengthened. The surgeon then has to make adjustments with the head to correct this. This adjustment occurs independent of the position of the stem in order to restore and obtain the proper leg length.

One-piece designs are typically formed from a solid piece of metal, such as titanium, stainless steel, or cobalt chromium alloys. As such, the stem, proximal body, and neck are integrally formed together. Even though the implants are manufactured in a wide range of shapes and sizes, the individual elements cannot be separately altered or sized since no changes or adjustments occur between the elements themselves.

The largest cause of early failure and revision surgery in hip replacement is dislocation of the head from the socket caused by instability of soft tissues surrounding the hip joint which is caused mostly by lack of head center distance to that of the femoral axis (called offset) or improper alignment of the femoral stem relative to the acetabular cup. This prevents the surgeon from being able to stabilize the joint adequately. The joint could be tensed by either using stems that offer adequate offset or the surgeon can use heads that would lengthen the leg which is not preferred. In an effort to resolve this, manufacturers are offering stem systems with smaller and larger offsets. Some achieve the offset by changing the neck angle. This method is not well accepted as the leg length cannot be maintained especially when heads with shallower taper are used to adjust leg length. The favored method of increasing offset is using systems that provide parallel shift of necks, i.e. the neck angle is preserved while the location of the neck is shifted further away from the centerline of the femoral axis. In an effort to reduce inventory and provide surgeon with more flexibility manufacturers are offering various modular neck and stem components. Another issue with unitized designs is inability to match the neck on the stem with the patient's natural femoral neck anteversion (forward rotation) that is widely variable from patient to patient. An inaccurate anteversion can cause a decrease in range of motion, neck impingement, excessive component wear, and lead to subluxation or even dislocation.

In contrast to one-piece designs, modular designs have some components that are interchangeable. Specifically, modular hip prostheses are formed from individual, separate components that are interchangeable and connectable together. The amount of modularity and degree of adjustability between components varies widely depending on the design and manufacturer of the prosthesis. A prosthesis in which the stem and neck are a unitary device requires that the surgeon have a large quantity of prostheses available to provide correct bio-mechanical function of the prosthesis with the patient. It is very costly to manufacture and maintain a large inventory of prostheses and, despite the number of prostheses available, quite often the appropriate stem size does not provide the neck offset, angle or anteversion required to best fit the patient.

One of the first modular designs in production is shown in U.S. Pat. No. 4,846,839 entitled "APPARATUS FOR AFFIXING A PROSTHESIS TO BONE" to Noiles. In one embodiment, a proximal body that connects to a distally fixed to bone stem and neck integrally formed together is described. The stem and neck component is angularly adjustable to the proximal sleeve allowing for 360 degree version control. Also different stem and neck components are possible which allow for horizontal offset shift which is favored by surgeons. However use of such system would require a perpendicular femoral neck resection for the placement of the proximal sleeve and for the surgeon to be able to clear femoral bone when placing the stem and neck portion in a rotated position. A perpendicular neck resection would result in a larger bone removal from the neck, which has been shown to reduce proximal fixation and initial stability of the stem in bone which is not favored. As such, this type of design has to augment proximal fixation with distal fixation and load transfer.

More recently, modular prostheses have been designed to overcome the low neck resection problem. Ceramascoli describes in U.S. Pat. No. 4,957,510, "HIP PROSTHESIS STRUCTURE ADAPTED FOR EASY FITTING TO PATIENT COXO-FEMURAL ARTICULATION", a modular neck and stem configuration. In such design the neck resection angle is oblique and preserves femoral bone which provides a favorable situation by preserving bone and achieving more of a proximal fixation. However, the tapered junction does not allow design of a neck portion that can provide parallel offset shifts. Many manufacturers have introduced designs with this feature and are forced to accept offset increase by method of neck angle change which is not favored by surgeons. As such these designs have not been well accepted in the market.

SUMMARY OF THE INVENTION

It is a major object of the invention to provide method and apparatus overcoming the above referenced problems and difficulties encountered during hip replacement surgery. Basically, the improved hip replacement process of the invention includes the steps:

a) providing a selected size generally longitudinally extending stem and laterally angled neck, the stem received endwise into a recess in an elongated femur, there being a ball on the neck, b) a size selected base carrying the neck, the base and stem having a non-circular tongue and groove interfit connection to resist relative rotary displacement therebetween, said connection defining a generally longitudinal axis, c) fitting said ball in a socket on a hip bone, to pivot in the socket, said selection of base and neck, and tongue and groove connection between the size selected base and stem, enabling accurate pivoting of the ball.

The non-circular interfit is typically defined by at least one oval cross section of the tongue and groove, at the interfit location, as further may be defined by multiple oval lobes. This allows adjustment of the tongue and groove connection after the stem is fully inserted into the elongated recess in the femur. As will be seen, a block configuration of the base fitting in a pocket having tapered side flanges, and bottom and end walls, secures the base in position, and allows for securement of a range of different length bases, with selected neck positioning.

A set of neck and ball units may be provided, and of selectively and progressively different size and/or shape configurations, and said providing step includes selecting one of said units corresponding to most accurate fitting of the ball with the socket. The most accurate fitting includes choosing and employing the one unit that provides the most accurate intermediate connection between the femur and the ball seating in the socket for ball pivoting in the socket and for correct leg length.

Another object is to provide, in combination with the ball,
a) a base in the form of a block connected with the neck,
b) and a pocket in an upper end of the stem, and characterized as sized to receive the base,
c) the pocket having opposite internally facing sides to closely receive opposite outwardly facing sides of the base therebetween, and having an open top for downward reception of the base,
d) the pocket having an open front for selective reception of each of a set of different length bases to openly extend forwardly, beneath the level of said neck.

A further important object is provision for reduced cost of providing a needed set of varying dimension stems for use, fewer such expensive stems being needed in inventory.

As will be seen, the invention provides freedom during surgery, to restore patient leg length and ball and socket offset, by choice of stem size.

These and other objects and advantages of the invention, as well as the details of an illustrative embodiment, will be more fully understood from the following specification and drawings, in which:

DRAWING DESCRIPTION

FIG. 5 is a side elevational view of the ball and neck unit assembled to the stem;

FIG. 6 is a top plan view of the FIG. 5 assembly;

FIG. 19 is a side elevational view of assembled components;

FIG. 20 is a side elevational view of the stem of FIG. 19;

FIGS. 21 and 22 are side elevational views of the two base, neck and ball components of FIG. 19;

FIG. 23 is an exploded, angled view of stem, base, neck and ball components;

FIGS. 30-33 are side, front, rear and top views of selected assembly components wherein the neck extends at an angle Δ relative to a plane bisecting the stem;

DETAILED DESCRIPTION

Figure 1:
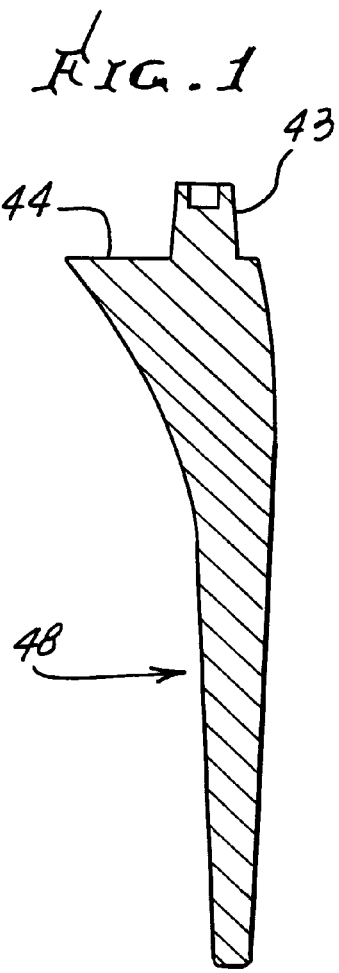
FIG. 1 is a section taken in elevation through a representative stem to be inserted and retained in an elongated recess in the femur.
Figure 3:
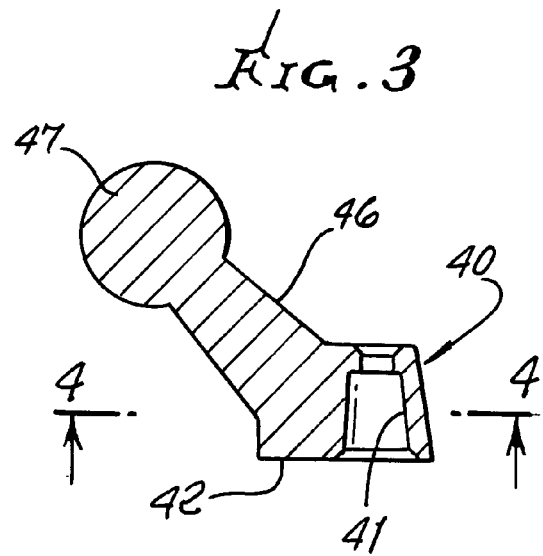
FIG. 3 is a section taken in elevation through a representative selected neck and ball, to be connected to the FIGS. 1 and 2 stem, the neck and ball unit selected from a set of such devices of progressively different size, to best connect the socket to the femur, for elimination of dislocation problems.

Referring first to FIGS. 19-24, hip replacement components shown include a selected size generally longitudinally extending stem 10 having an enlarged upper end 10*a*, and a tapered lower end 10*b*, to fit endwise in a corresponding recess 11 formed in a leg bone, i.e. femur 12. One laterally and upwardly extending neck 13 carrying a ball 14 is shown in FIG. 21, and these elements are also shown in FIG. 22. One size selected base 15 carries the neck and ball in FIG. 21, and another size selected base 16 carries the neck and ball in FIG. 22, the dimensions and angularity of the necks 13 in FIGS. 21 and 22 are the same, and the carried ball sizes are the same.

Base 15 is generally of rectangular block shape and has a bottom horizontal wall 18, top wall 19, an upright right end wall 20, and an upright left end wall 21. The dimension between walls 20 and 21 is indicated as $x_1$. Base 16 is also generally of rectangular block shape, having a bottom horizontal wall 22, top horizontal wall 23, upright right end wall 24, and upright left end wall 25. The dimension between walls 24 and 25 is indicated at $x_2$. Of importance is that $x_2 > x_1$.

Multiple such blocks are typically provided each having a different horizontal dimension between right end and left end walls, whereby a selected dimension offset between the left end wall and an upright plane P through the ball center, and neck version, is or are easily and quickly chosen by the surgeon for use, to best match the need for such an offset and version during hip replacement surgery, and to enable final adjustment of offset and version after the stem is implanted. Also, a much reduced inventory of base, neck and ball units is enabled or required. FIG. 19 shows the varying offsets provided by the two bases 15 and 16.

It will be noted that when the base is installed in the stem, it fits widthwise closely in the pocket or notch 30 formed at the top of the stem, with bottom wall 18 seating on pocket bottom wall 31, and left end wall 21 seating against notch upright wall 32. A downward projection or tongue 34 from base bottom 18 fits closely in an anchoring and matching groove or recess 35 sunk in pocket bottom wall 31. This is facilitated by the downward taper 34*a* of the tongue 34. That anchoring interfit functionally resists and prevents upward counter-clockwise prying or tilting of the base in the pocket as torque or force is transmitted to the ball in its hip socket. Taper of tongue 34 also permits upward escape of liquid such as blood, from the pocket, during interfit.

It will be noted that successive bases, in inventory, may have the same height dimension, as at $x_5$ for base 15, and $x_6$ for base 16; or, such height dimension may successively increase or decrease, whereby the height dimension between the ball center 14*a* and the base bottom wall at the pocket bottom wall, varies correspondingly, enabling quick choice of best match of the ball to its socket, from a minimum inventory.

FIG. 23 shows that the widths $x_1$ of the bases 15 and 16 are the same, to fit in the corresponding width $x_8$ pocket. The pocket has an upper external face 36 that is downwardly and rightwardly angled, to allow the selected base to project rightwardly from the pocket, and also to allow substantial extents of the base opposite side walls 37 and 38 to be frictionally enveloped by the stem flanges 39 and 39' at opposite sides of the pocket. The base may be frictionally or adhesively received in the pocket if desired.

Figure 2:
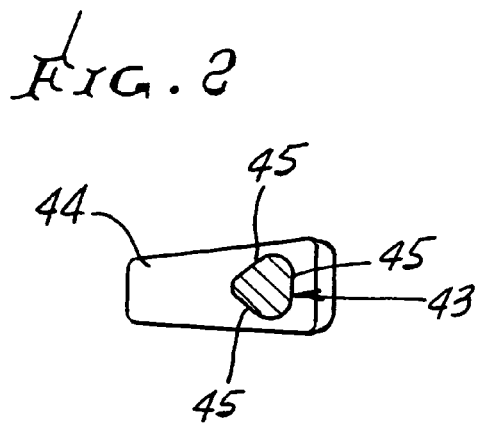
FIG. 2 is a top plan view of the FIG. 1 stem.
Figure 4:
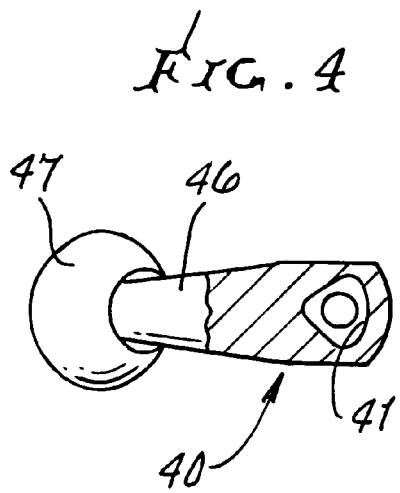
FIG. 4 is a section taken on lines 4-4 of FIG. 3.

FIGS. 1-4 show elements like those of FIGS. 18-22, except that the base 40 has a tapered recess 41 extending upwardly from bottom wall 42; to interfit a tongue or projection 43 is integral with the top 44 of stem. Tongue 43 is upwardly tapered and fits into the recess. As shown in FIG. 2, the tongue has a non-circular cross section, with lobes 45 that fit in the similarly shaped recess. FIGS. 5 and 6 show the neck assembled onto the stem. Neck 46, ball 47 and stem 48 elements are also shown.

Figure 7:
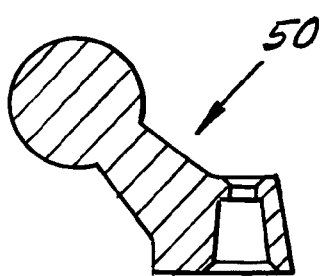
FIGS. 7 and 8 show in section two modular ball and neck units of a set of progressively different size or shape such units.
Figure 8:
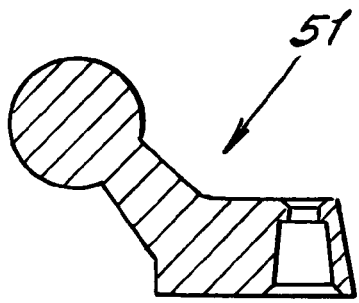

FIGS. 7 and 8 show in section two modular ball and neck units 50 and 51 of a set of progressively different size or shape such units.

Figure 9:
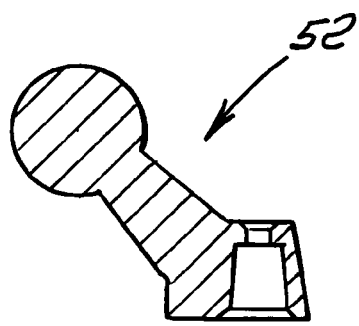
FIGS. 9 and 10 show in section two modular ball and neck units of a set of progressively different size or shape such units.
Figure 10:
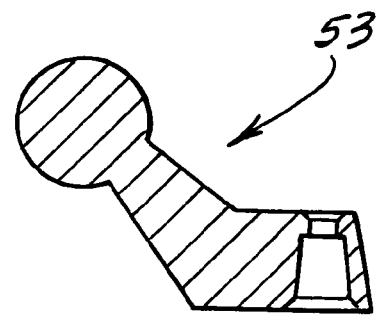

FIGS. 9 and 10 show in section two modular ball and longer neck units 52 and 53 of a set of progressively different size or shape such units.

Figure 11:
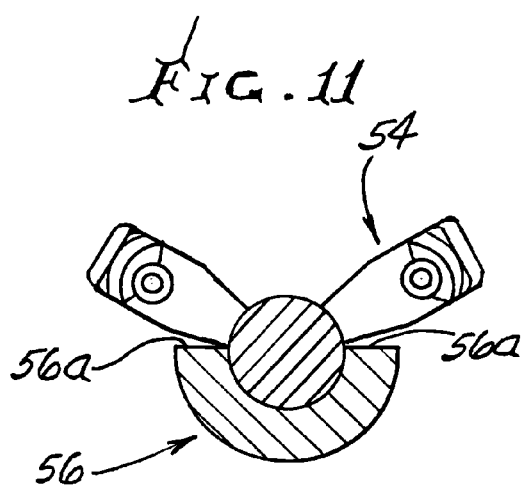
FIGS. 11 and 12 are sections taken through a ball and socket, and stems, of two assemblies showing provision of increased ball pivoting, in FIG. 12.
Figure 12:
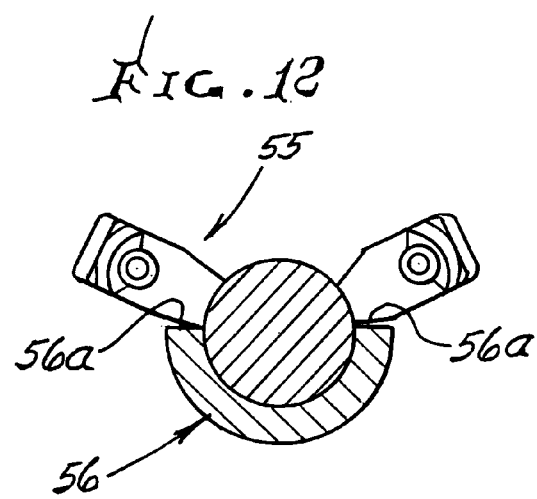

FIGS. 11 and 12 are sections taken through a ball and socket, and stems, of two assemblies 54 adn 55 showing provision of increased ball pivoting, in FIG. 12. Hip socket 56 edges 56*a* limit such pivoting.

Figure 13:
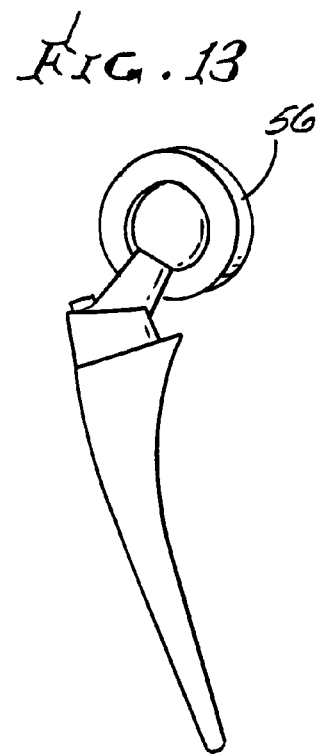
FIGS. 13 and 14 are perspective views showing stems incorporating elements of the invention.
Figure 14:
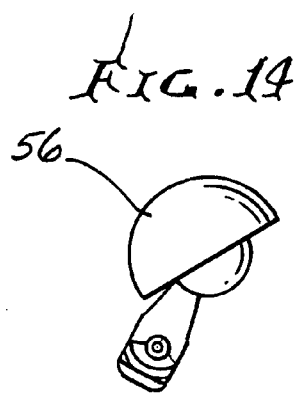

FIGS. 13 and 14 are perspective views showing stems, necks and balls incorporating elements of the invention.

Figure 15:
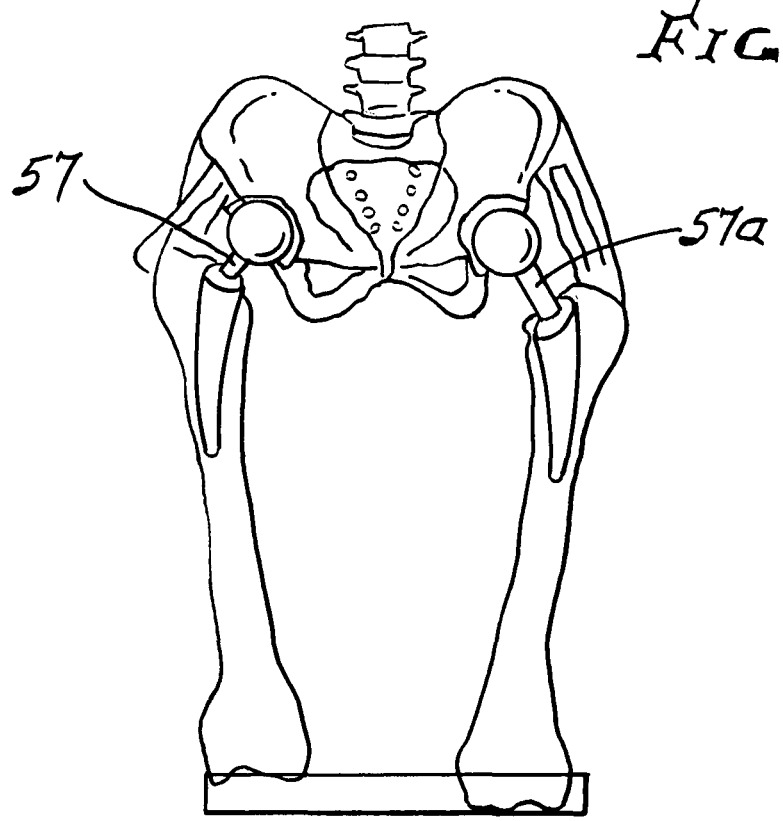
FIG. 15 is a view of hip installation of stem and ball elements.
Figure 15A:
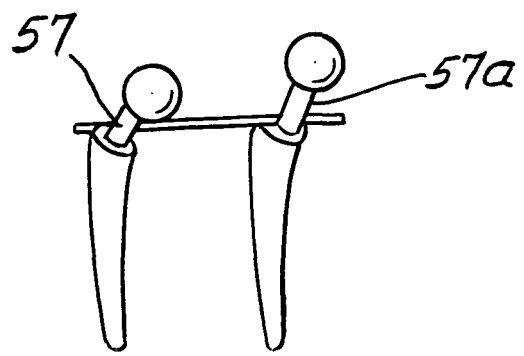
FIG. 15a shows two different neck lengths.

FIG. 15 is a view of hip installation of stem neck and ball elements; and FIG. 15*a* shows two different neck lengths 57 and 57*a*, as used in FIG. 15.

Figure 16:
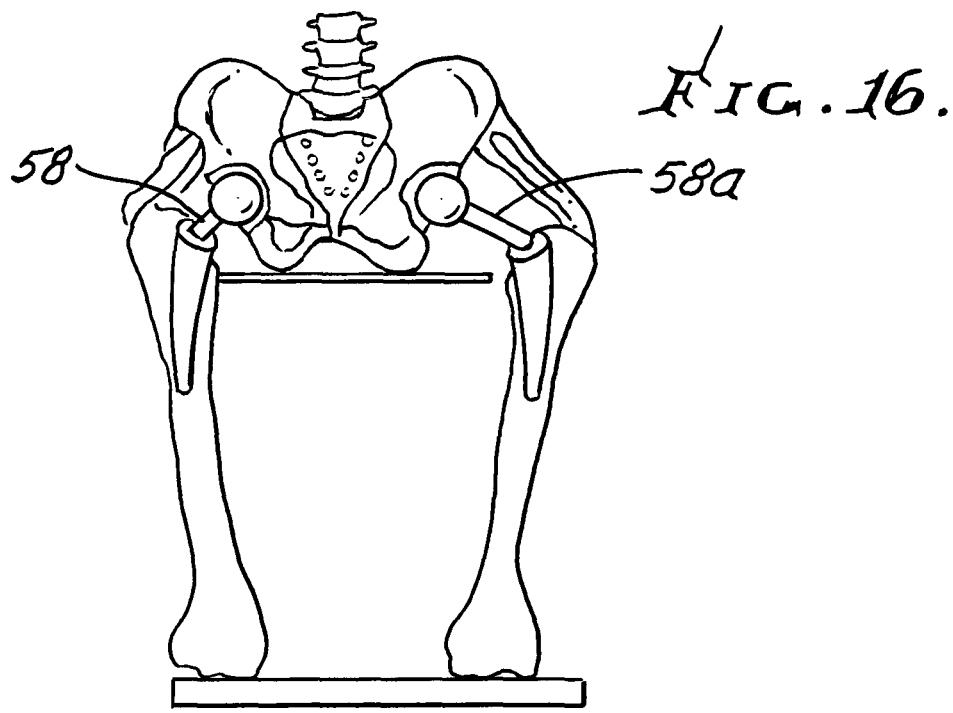
FIG. 16 shows installation of two different neck lengths, in hip structures.
Figure 16A:
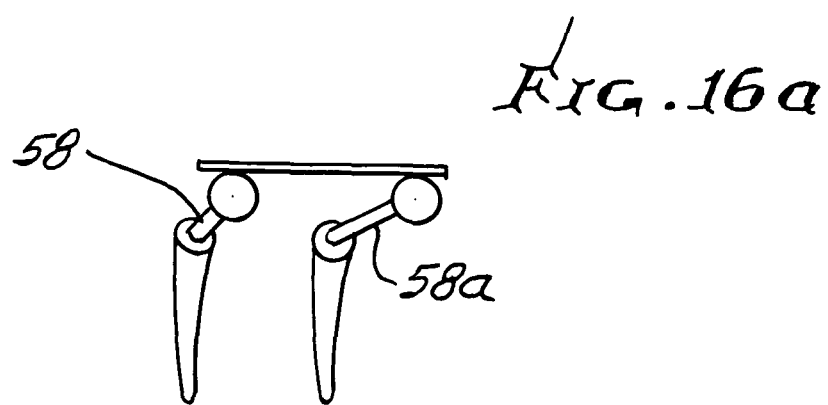
FIG. 16a shows the neck, ball and stem elements of FIG. 16, prior to installation.

FIG. 16 shows installation of two different neck lengths 58 and 58*a*, in hip structures; and FIG. 16*a* shows the neck, ball and stem elements of FIG. 16, prior to installation.

Figure 17:
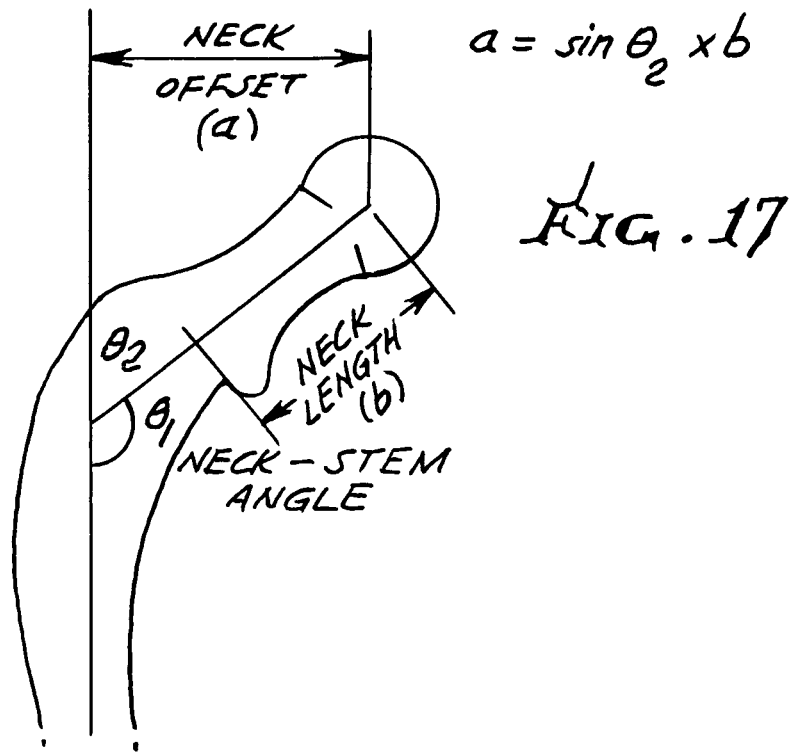
FIGS. 17 and 17a are geometrical representations.
Figure 17A:
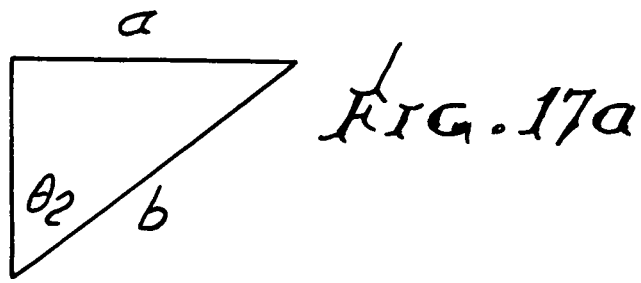

FIGS. 17 and 17*a* are geometrical representations showing neck connection to a stem, and dimensioning in relation to a triangle having dimensions as seen in FIG. 17.

Figure 18A:
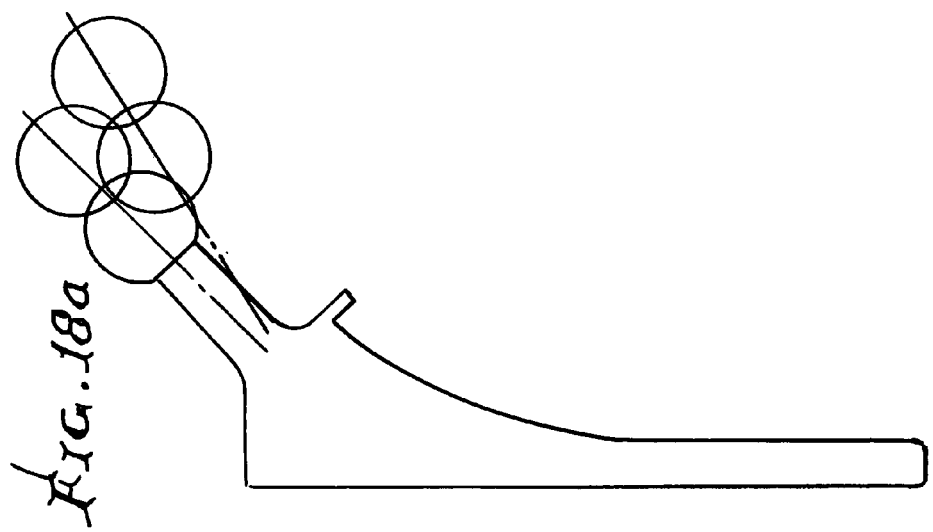
FIGS. 18 and 18a are geometrical representations.
Figure 18:
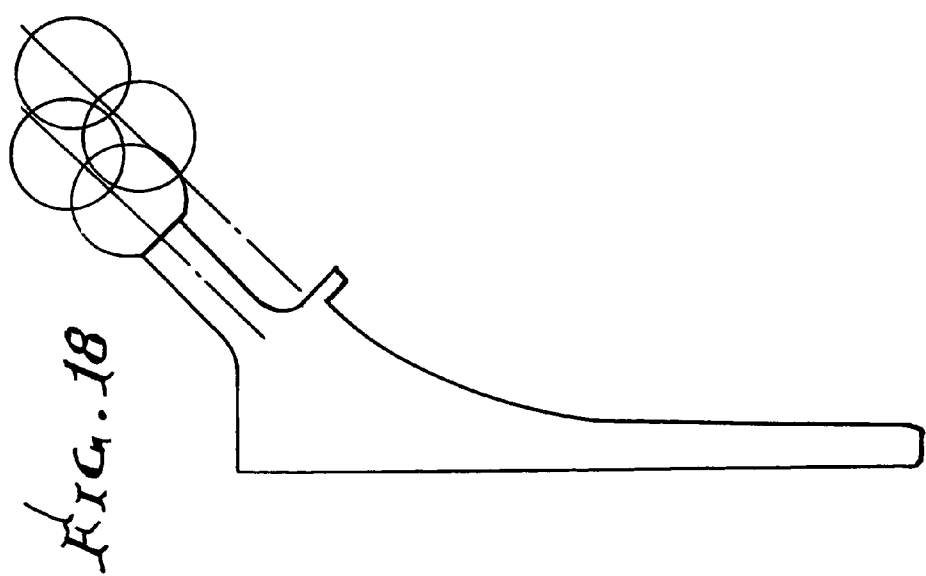
Figure 24:
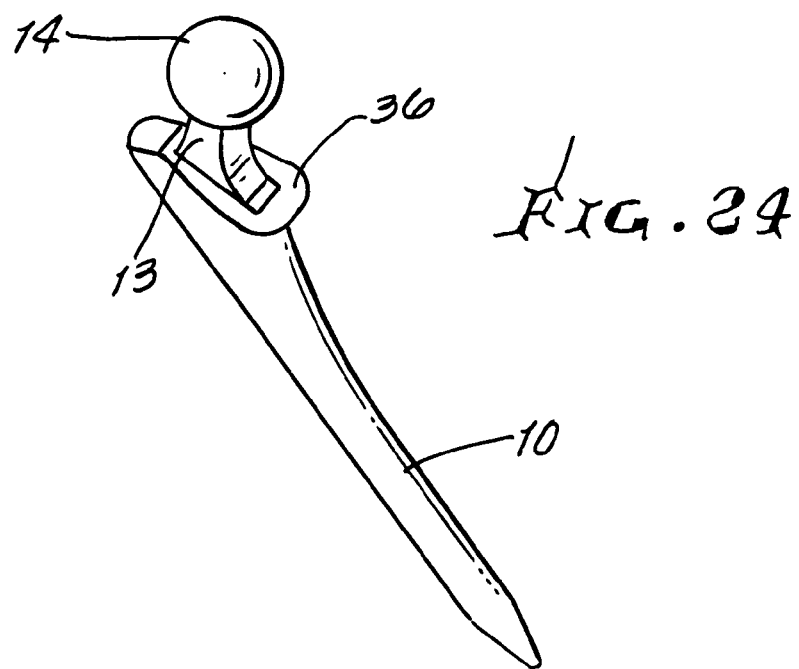
FIG. 24 is an assembled angled view of the FIG. 23 components.
Figure 25:
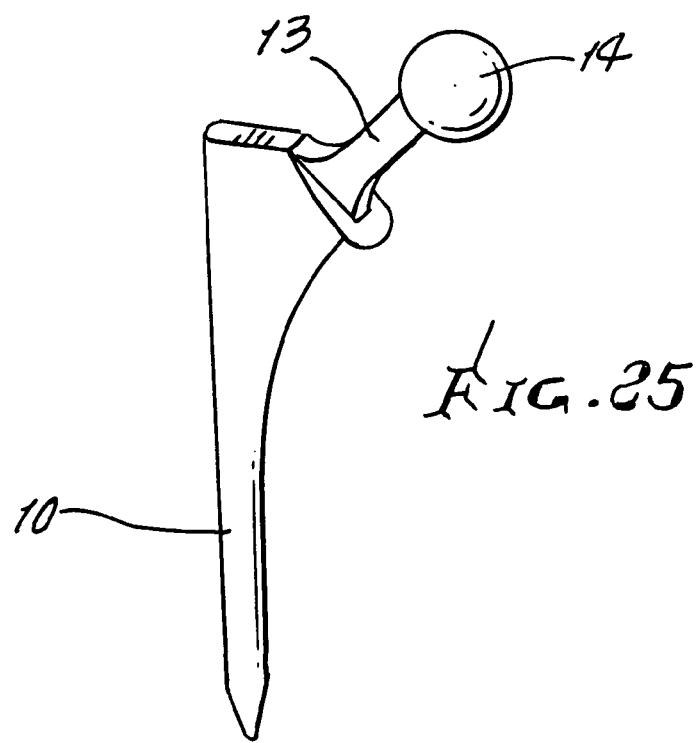
FIG. 25 is an assembled side view of the FIG. 23 and FIG. 24 components.

FIGS. 18 and 18*a* are geometrical representations of different neck and ball comparative configurations, as referenced.

Figure 26:
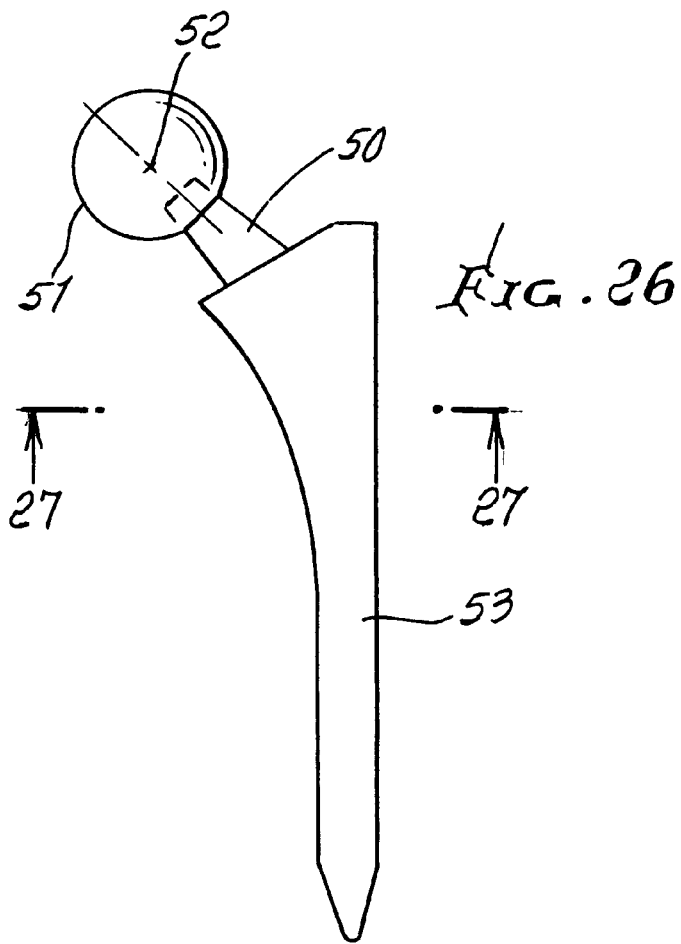
FIG. 26 is a side view of a modified assembly incorporating the invention.
Figure 27:
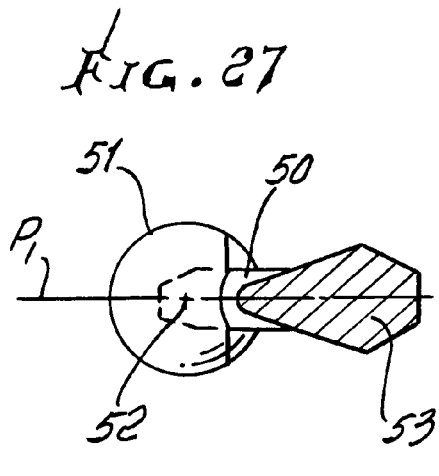
FIG. 27 is a section taken on lines 27-27 of the FIG. 26 assembly.
Figure 28:
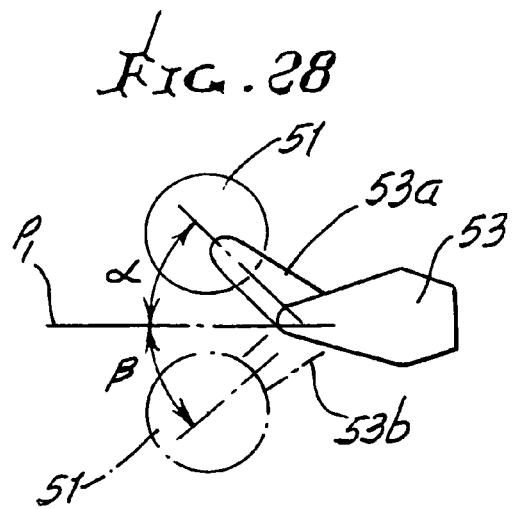
FIG. 28 is a top plan view, like FIG. 27, but showing the neck in either anteverted position, or retroverted position.

FIGS. 26 and 27 show the selected neck 50 and ball 51 in neutral position, with the ball center 52 in the same plane $P_1$ that bisects the stem 53. FIG. 28 is like FIG. 27 but shows the selected neck 53*a* angled at α from plane $P_1$, i.e. in antiverted position. Also shown, as an alternate, is the selected neck 53*b* angled at β from plane $P_1$ i.e. in retroverted position. A set of necks of different angular values α and β is usable, for selection by the physician.

Figure 29:
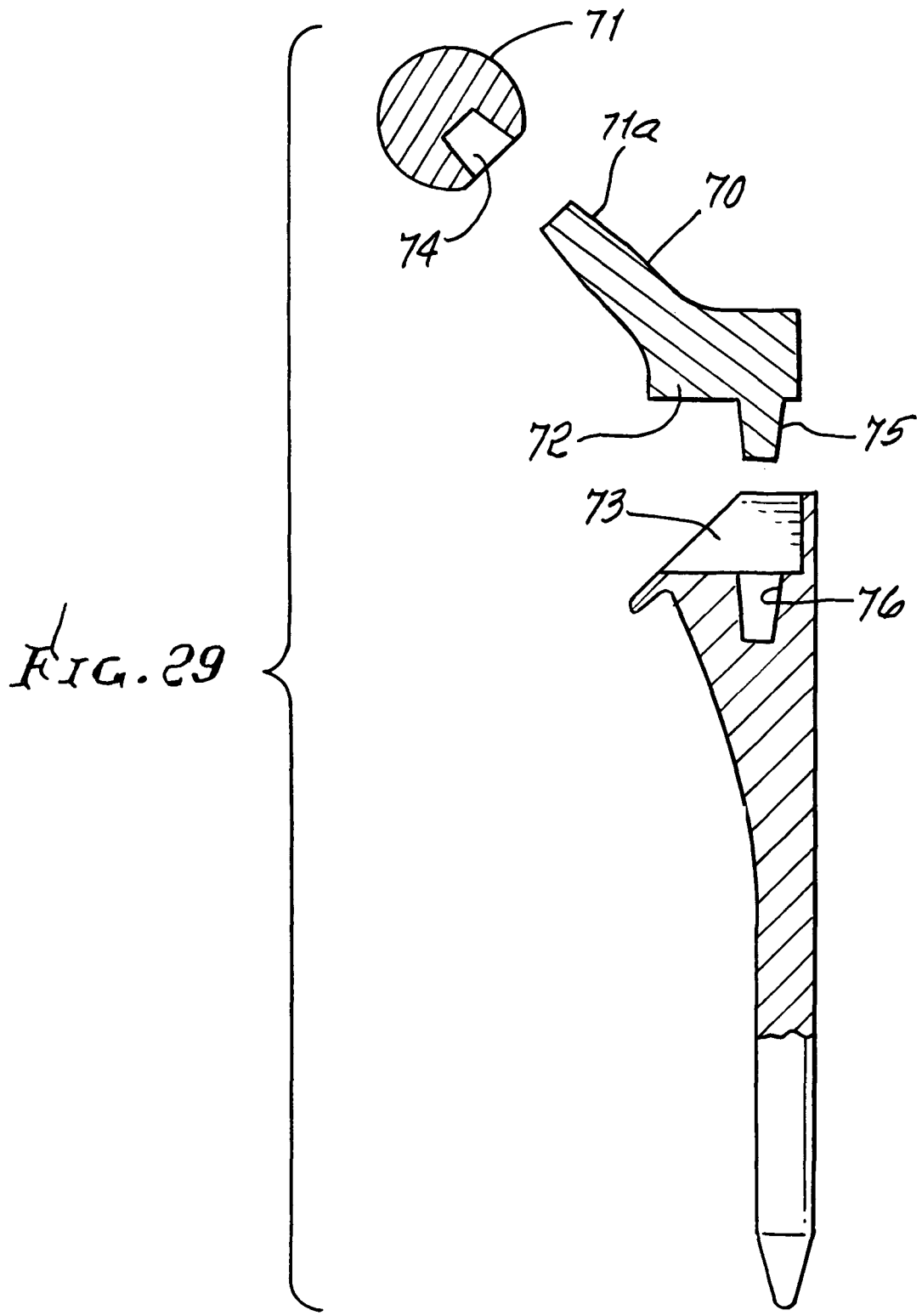
FIG. 29 is a section taken through a modular neck and base that fits into a stem pocket, and showing a modular ball that fits onto a neck tapered end.

FIG. 29 is a section taken through a modular neck and ball 70 and 71, and a base 72 that fits into a stem pocket 73, as in FIGS. 19-22 and showing a modular ball 71 with a tapered recess 74 that fits onto a neck tapered end 71*a*. See also tapered interfitting tongue and groove elements 75 and 76.

FIGS. 30-33 are side, front, rear and top views of selected assembly neck, ball, base and stem components 80-83 wherein the neck extends at an angle Δ relative to a plane $P_2$ bisecting the stem providing selected offset.

Figure 34B:
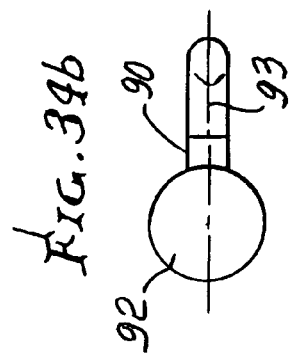
FIGS. 34a-34c are side, top and bottom views of a neck, base and ball assembly in neutral positions wherein the same plane bisects these elements.
Figure 34A:
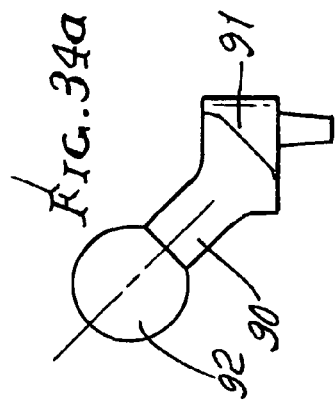
Figure 34C:
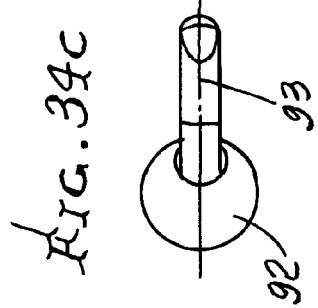

FIGS. 34*a*-34*c* are side, top and bottom views of a neck, base and ball element 90-92 assembly in neutral positions wherein the same plane 93 bisects these elements.

Figure 35B:
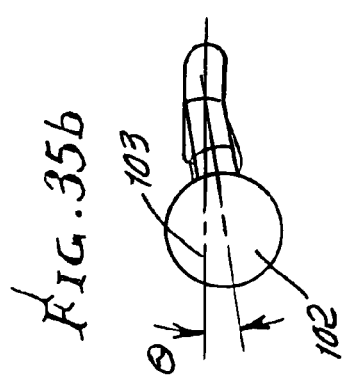
FIGS. 35a-35c are side, top and bottom views of neck, base and ball assembly elements, as in FIG. 1, but wherein the neck is angled relative to a plane bisecting the bottom of the base.
Figure 35A:
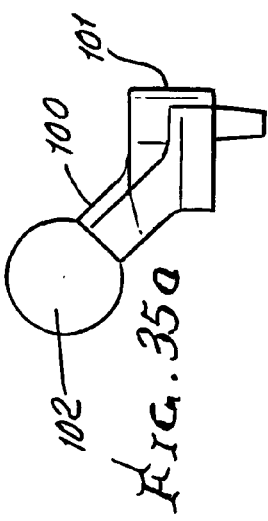
Figure 35C:
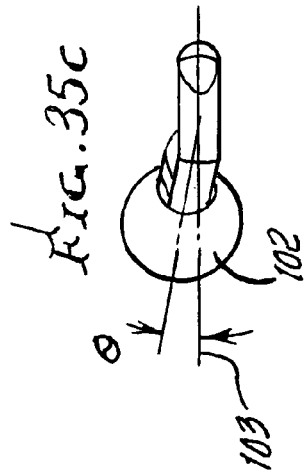

FIGS. 35*a*-35*c* are side, top and bottom views of neck, base and ball assembly elements 100-102, as in FIGS. 34*a*-34*c*, but wherein the neck is angled at angle Ø relative to a plane 103 bisecting the bottom of the base.

Figure 36B:
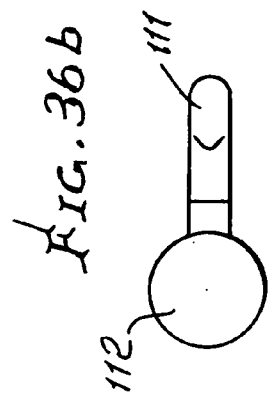
FIGS. 36*a*-36*c* are side, top and bottom views of neck, base and ball assembly elements, as in FIG. 1, but wherein the base is elongated to provide greater offset.
Figure 36A:
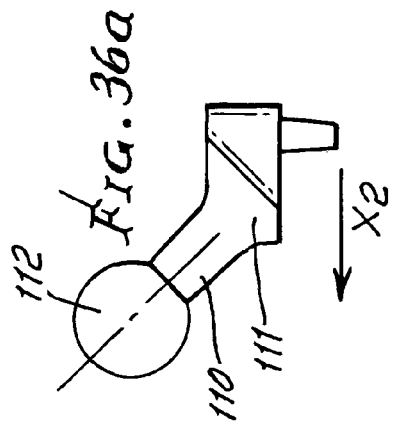
Figure 36C:
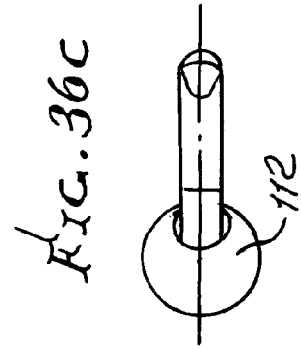

FIGS. 36*a*-36*c* are side, top and bottom views of neck, base and ball assembly elements 110-112, as in FIGS. 34*a*-34*c*, but wherein the base is elongated in direction $x_2$ to provide greater effect for the ball relative to the stem.

With respect to prior devices, impingement of the neck of the stem on to the rim of the socket is a cause of poor outcomes of prosthetic hip arthroplasty; it can lead to instability, accelerated wear, and pain. Impingement is influenced by prosthetic design, component position, biomechanical factors, and patient variables.

Impingement of the neck of the stem on to the rim of the socket may cause dislocation of the total hip prosthesis. Evidence linking impingement to dislocation and accelerated wear comes from implant retrieval studies. Implantation of the stem in a low anteversion has been shown to a clinically relevant reduction of the range of motion due to impingement and dominated in the group with dislocations. Operative principles that maximize an impingement-free range of motion include correct combined acetabular and femoral anteversion and an optimal head-neck ratio.

Operative techniques for preventing impingement include medialization of the cup to avoid component impingement and restoration of hip offset and length to avoid osseous impingement.

Impingement of the neck on the rim of the cup is minimized by inserting the femoral component in 10° to 20° of anteversion. However due to patient anatomy and femoral bone structure it is not always possible to implant the stem and the cup in a desired angular range of anteversion. As such it is important to have an implant system that allows for selective implantation of the stem portion independent of the version of the neck portion.

What is claimed is:

1. In a human hip replacement method, the steps that include:
   a) providing a selected size generally vertically extending stem and laterally angled neck, the stem received into a recess in an elongated femur, the neck adapted to support a ball,
   b) a size selected first base carrying the neck, the base and stem having a non-circular tongue and groove interfit connection to resist relative rotary displacement therebetween,
   c) fitting a selected ball on an open end of said neck,
   d) there being an acetabular cup and insert socket being placed into an acetabulum,
   e) fitting said ball in the socket on a hip bone, to pivot in the socket, said selection of stem and neck, and tongue and groove connection between the size selected base and stem, enabling accurate pivoting of the ball in the socket,
   f) said neck extending upwardly and angularly relative to an upper horizontal surface of the base, and the base has a lower horizontal surface receivable by the stem, the upper and lower horizontal surfaces having selected vertical spacing therebetween,
   g) the base having front and rear endwise horizontally spaced end surfaces with selected spacing therebetween, the neck extending frontally and upwardly and above front to rear endwise spaced surfaces, said spacing between the front to rear endwise spaced surfaces selected for best fit of the ball into the socket,
   h) providing a second base characterized in that said first and second bases each have like sized front and rear upright substantially parallel endwise spaced end surfaces, and
opposite side surfaces which are substantially parallel, the second base being endwise longer than the first base between respective end surfaces thereof, the second base also supporting a ball carrying neck sized the same as the first base neck, said step e) fitting of the ball in the socket facilitated by selectively employing one of the first and second bases for reception into a stem formed pocket, which is open ended to receive said bases.

2. The method of claim 1 wherein said connection is provided to locate said non-circular tongue and groove interfit extending vertically.

3. The method of claim 1 including assembling said tongue and groove interfit connection in conjunction with said stem fully inserted into said recess in the femur.

4. The method of claim 1 including relatively positioning said tongue and groove interfit to support said ball at selected angularity relative to a longitudinal axis of the stem.

5. The method of claim 4 including assembling the ball into the socket after relative positioning of the interfit is completed.

6. The method of claim 1 including providing a set of neck units, of selectively and progressively different shape configurations, and ball units that can fit or are fitted onto said neck units, and selecting one of said neck and ball units corresponding to most accurate fitting of the ball with the socket.

7. The method of claim 6 wherein said most accurate fitting includes relative longitudinal and rotative displacement of the ball relative to the socket.

8. The method of claim 1 wherein the base and neck have integral interconnection.

9. The method of claim 1 wherein the neck is angled relative to the base such that the neck can provide largest possible range of angular motion before it impinges on an edge of the socket in all directions.

10. The method of claim 1 including a set of said bases characterized by said spacing between said end surfaces thereof being selectively different.

11. The method of claim 1 wherein each base has rectangular block configuration.

12. The method of claim 11 wherein the stem forms said pocket receiving the first base between pocket flanges, the pocket being open at one end to receive different and selected length bases.

13. The method of claim 1 wherein the neck is provided to have one of the following:
   i) an antiverted angularly extending position relative to the first or second base,
   ii) a retroverted angularly extending position relative to the first or second base,
   iii) a neutral extending position relative to the first or second base.

* * * * *